United States Patent [19]

Kaneko

[11] Patent Number: 4,920,498

[45] Date of Patent: Apr. 24, 1990

[54] METHOD OF PROCESSING AND ANALYZING ELECTROPHORETIC IMAGE, AND METHOD OF DISPLAYING ELECTROPHOREGRAM AND A MEDIUM FOR RECORDING ELECTROPHOREGRAM

[75] Inventor: Nobutaka Kaneko, Hachioji

[73] Assignee: Olympus Optical Co., Ltd., Japan

[21] Appl. No.: 893,814

[22] Filed: Aug. 6, 1986

[30] Foreign Application Priority Data

| Aug. 17, 1985 | [JP] | Japan | 60-180031 |
| Aug. 17, 1985 | [JP] | Japan | 60-180032 |
| Aug. 27, 1985 | [JP] | Japan | 60-186533 |
| May 28, 1986 | [JP] | Japan | 61-122883 |

[51] Int. Cl.$^5$ .................... G06F 15/42; C25D 13/06
[52] U.S. Cl. ............................... 364/497; 204/180.1; 204/183.3; 364/413.02; 364/518
[58] Field of Search ............... 364/518–521, 364/497, 550, 496, 413.02; 204/183.3, 180.1, 299 R, 300 R

[56] References Cited

U.S. PATENT DOCUMENTS

| 4,504,920 | 3/1985 | Mickowski | 364/521 |
| 4,638,456 | 1/1987 | Elias et al. | 364/415 |
| 4,666,577 | 5/1987 | Yamamoto et al. | 204/183.3 |
| 4,666,578 | 5/1987 | Yamamoto | 204/183.3 |

OTHER PUBLICATIONS

"Messdatenerfassung bei der Elektrophorese", *Elektronik*, 1977, No. 5, pp. 67–71.

*Primary Examiner*—Kevin J. Teska
*Attorney, Agent, or Firm*—Arnold, White & Durkee

[57] ABSTRACT

Electrophoretic images of serum test sample and normal serum sample formed on the same substrate are photoelectrically scanned to derive a series of data samples relating to an electrophoregram of serum test sample and a series of data samples relating to a standard electrophoregram of normal serum sample. These electrophoregrams of test sample and normal sample are normalized such that they have a predetermined electrophoretic expansion length. Then normalized electrophoregrams of serum test sample and normal serum sample are displayed and printed in a superimposed manner. The normalized electrophoregram of serum test sample is further analyzed to detect specific peaks, valleys, bridgings and leadings to derive useful data for diagnosing various diseases.

34 Claims, 16 Drawing Sheets

FIG_2
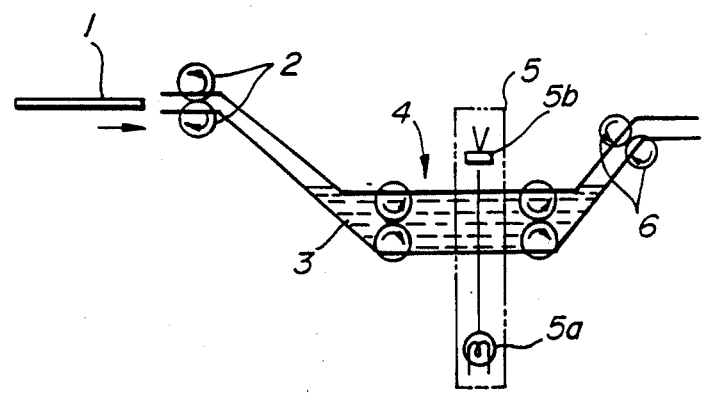
FIG_3
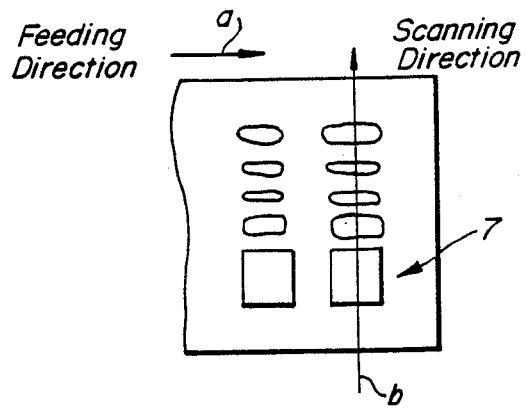

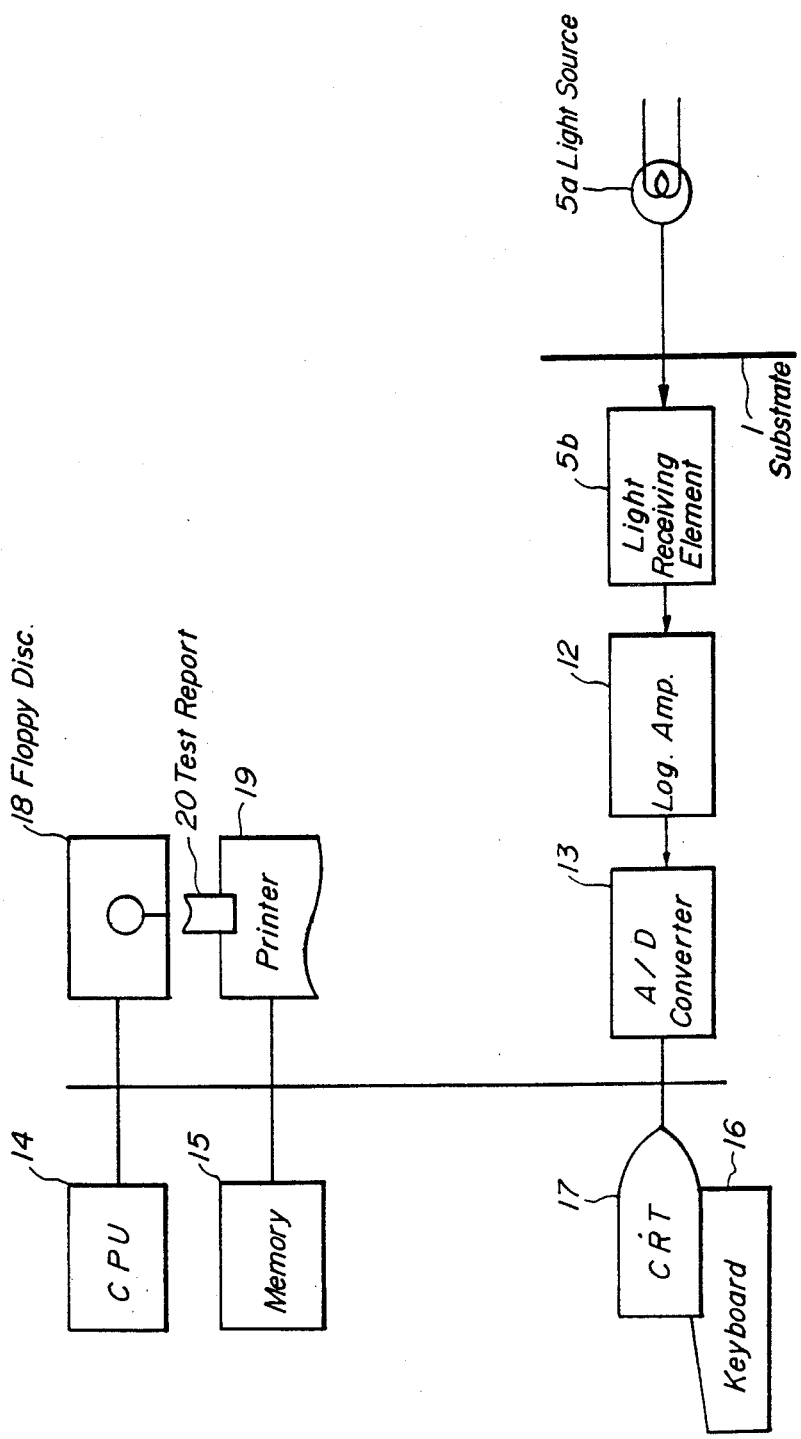

FIG_5
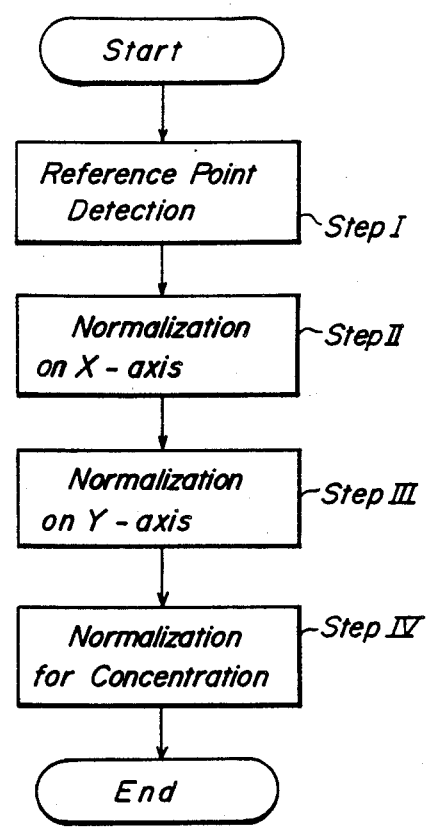
FIG_6
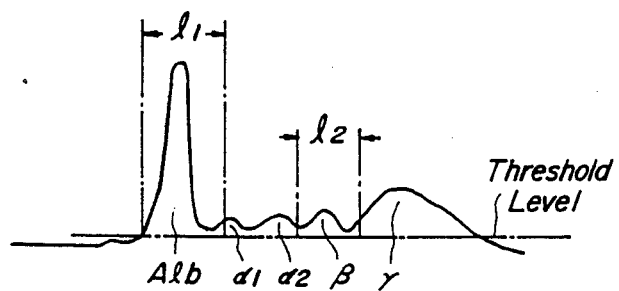

FIG_11A
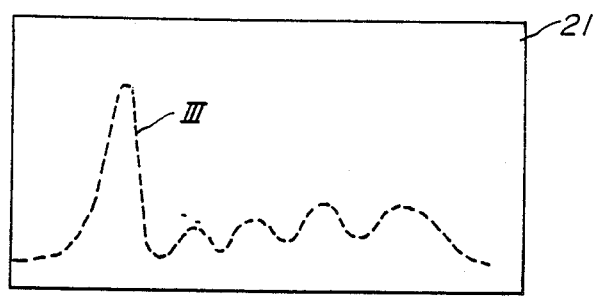
FIG_11B
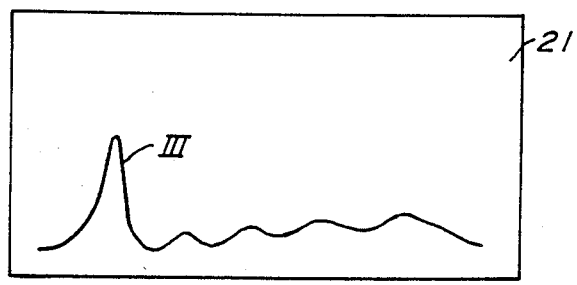
FIG_11C
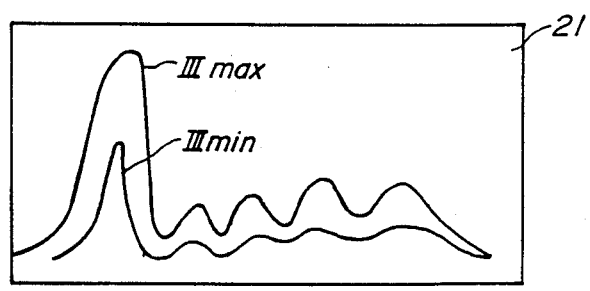

FIG_14
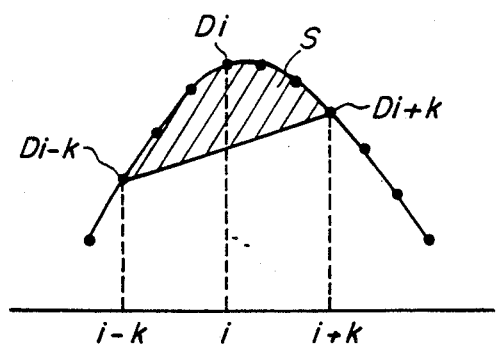
FIG_15
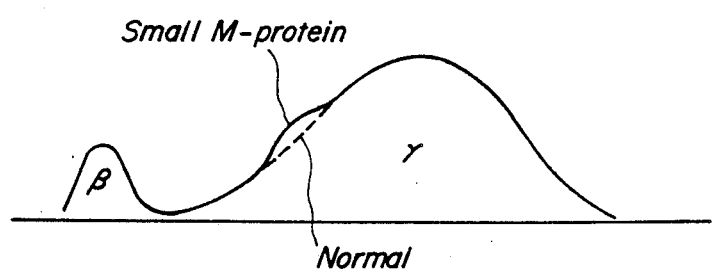
FIG_16
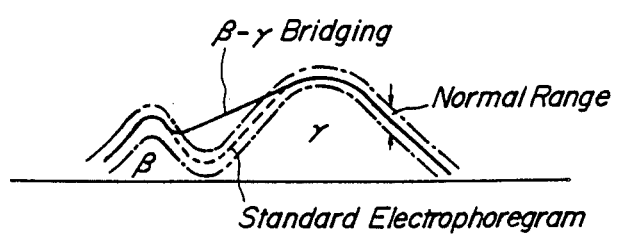

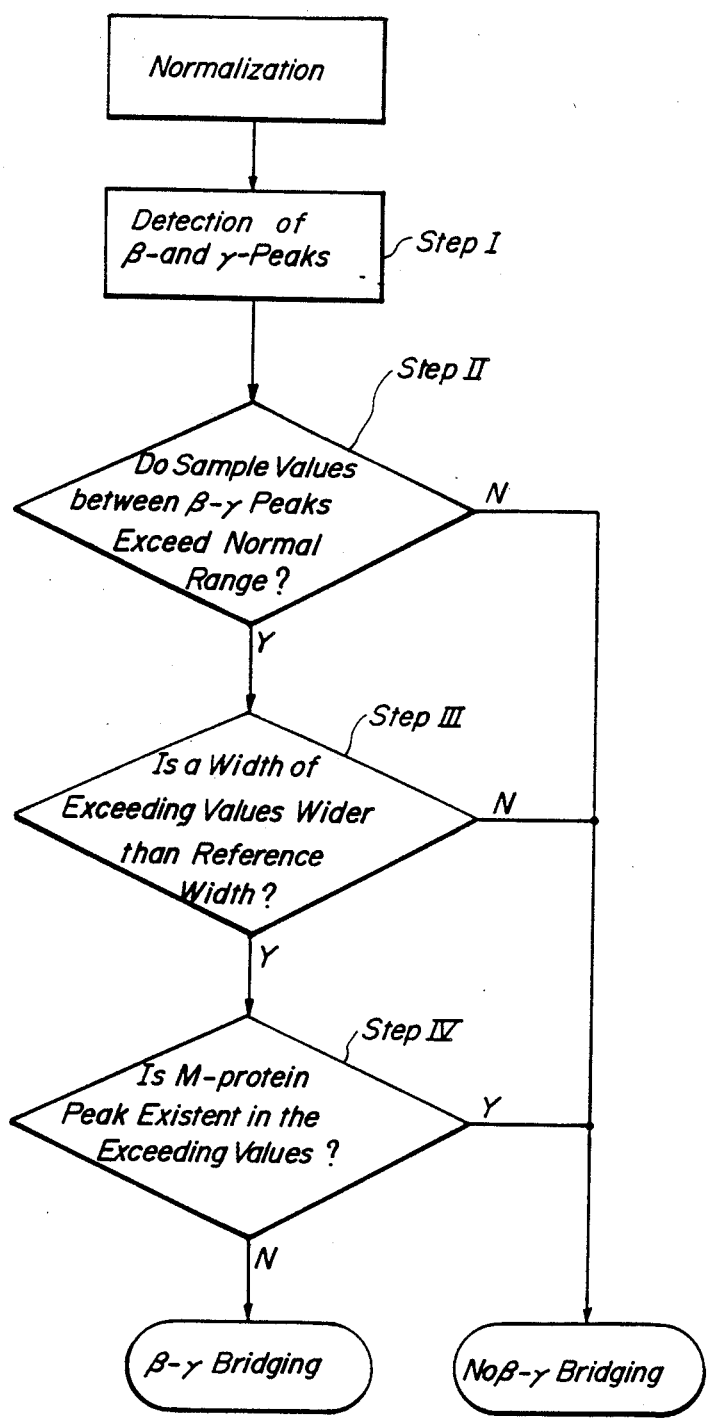
FIG_17

METHOD OF PROCESSING AND ANALYZING ELECTROPHORETIC IMAGE, AND METHOD OF DISPLAYING ELECTROPHOREGRAM AND A MEDIUM FOR RECORDING ELECTROPHOREGRAM

BACKGROUND OF THE INVENTION

Field of the Invention and Related Art Statement

The present invention generally relates to a technique for processing and analyzing an electrophoretic image.

Proteins contained in a serum sample have been analyzed by electrophoresis owing to the reason that electrophoresis can provide a lot of useful data for diagnosing various kinds of diseases. Therefore, nowadays electrophoresis for the serum sample has been widely effected as an item of the primary screening. The electrophoresis for a serum sample has been automated and has become a major test of analyzing various kinds of proteins contained in the serum sample. In an automatic electrophoretic apparatus, serum samples are applied on a substrate such as a cellulose acetate film by means of an applicator and are subjected to the electrophoretic process in an electrophoretic vessel for a given time. Then the substrate is dyed, decolored and dried, successively. Further the substrate is introduced into a densitometer containing a decalin and electrophoretic images of serum samples are made visible. Then these electrophoretic images are photoelectrically scanned by a light beam to obtain electrophoretic image signals. Next fraction percentages of albumin (Alb), $\alpha_1$-globulin ($\alpha_1$), $\alpha_2$-globulin ($\alpha_2$), $\beta$-globulin ($\alpha$) and $\gamma$-globulin ($\gamma$), a ratio A/G of the fraction percentage of albumin to a total percentage of the $\alpha_1$-, $\alpha_2$-, $\beta$- and $\gamma$-globulins, and absolute concentration values of these proteins are calculated and are printed on a test report together with an electrophoregram, i.e. densitogram. They are also displayed on a display device such as a cathode ray tube (CRT).

In the known electrophoretic apparatus, the electrophoregram is subjected to an automatic span control such that a peak of the albumin fraction which usually has the highest value assumes always a given constant level. In this case, variations in absolute values of respective substances could not be detected. Further, in the known method of analyzing and processing the electrophoretic image, it is difficult to find important data or information such as existence of monoclonal protein (M-protein), difference or variation in electrophoretic mobility and existence of specific waveforms such as $\gamma$-suppression, $\beta$-$\gamma$ bridging and leading. Therefore, in order to diagnose various kinds of diseases with the aid of the known electrophoregram, substantial skill of an expert is required. Variation in absolute values of the proteins may be detected from the electrophoregram by making an amount of a sample serum applied on the substrate always constant. However, in practice, it is very difficult to apply always the same amount of samples to the substrates, because a required amount of samples is quite small. Moreover, a length on the substrate over which the electrophoretic image is expanded varies to a large extent in dependence upon various factors of the electrophoresis.

In order to diagnose diseases from the displayed electrophoregram and values calculated from the fraction percentages, there is required substantial experience and skill which depend upon respective doctors and inspection examiners.

These days there have been proposed various attempts to diagnose diseases from analytical results obtained by the electrophoretic apparatus. FIG. 1 shows a flow chart illustrating steps of effecting a classification of diseases from the total amount of proteins and amounts of respective proteins calculated from the total amount of proteins and respective fraction percentages. In this process, specific waveforms or shapes of the electrophoregram such as M-protein, $\gamma$-suppression and $\beta$-$\gamma$ bridging have to be detected from the electrophoregram. However, in the known method since the electrophoregram is subjected to the automatic span control in such a manner that the peak point of the albumin fraction image having the highest value assumes a given constant level, it is very difficult to detect the above mentioned specific waveforms or shapes even for experienced and skilled doctors.

SUMMARY OF THE INVENTION

The present invention has for an object to provide a novel and useful method of analyzing and processing an electrophoretic image, which can provide an electrophoregram which represents concentration changes of respective substances in an accurate manner, and thus can offer useful data or information for diagnosing diseases.

It is another object of the invention to provide a method of displaying an electrophoregram by means of which variations in concentration of respective substances contained in samples can be easily and precisely judged, so that diseases can be diagnosed accurately, even if amounts of samples applied on substrates differ from each other and electrophoretic expansion lengths over which fraction images of sample substances extend on the substrates differ from each other.

It is another object of the invention to provide a record medium on which an electrophoregram can be recorded in superimposition with a standard electrophoregram of normal sample.

It is still another object of the invention to provide a method of indicating analytical results of electrophoretic analysis, in which data and information of an electrophoregram can be easily and accurately read out.

According to the invention, a method of processing an electrophoretic image obtained by subjecting a test sample to an electrophoresis comprises the steps of:

photoelectrically scanning the electrophoretic image of the test sample to derive an electrophoretic image signal;

sampling the electrophoretic image signal to derive a number of data samples;

detecting at least two reference points on the electrophoretic image in accordance with the data samples; and normalizing said data samples in such a manner that said at least two reference points are made coincident with at least two predetermined points on an electrophoregram having a predetermined electrophoretic expansion length.

According a further aspect of the invention, a method of displaying an electrophoregram obtained by subjecting a test sample to electrophoresis and by photoelectrically scanning an electrophoretic image of test sample comprises the steps of:

deriving a pattern related to a standard electrophoregram of normal sample;

normalizing an electrophoretic expansion length of the electrophoregram of test sample; and displaying the electrophoregram of test sample having the normalized electrophoretic expansion length and said pattern in a superimposed manner.

According to still another aspect of the invention, a method of displaying or printing results of the electrophoresis comprises the steps of:

normalizing an electrophoregram of test sample to derive a normalized electrophoregram of test sample;

comparing the normalized electrophoregram of test sample with a standard electrophoregram to derive at least one pattern; and displaying or printing said normalized electrophoregram of test sample and said pattern one upon the other such that respective measuring points of the pattern are aligned with corresponding measuring points of the normalized electrophoregram of test sample.

BRIEF DESCRIPTION OF THE DRAWINGS

FIG. 2 is a schematic view illustrating a densitometer for scanning an electrophoretic image formed on a substrate;

FIG. 3 is a schematic view illustrating a manner of scanning the electrophoretic image;

FIG. 4 is a block diagram depicting an embodiment of an apparatus for performing the method according to the invention;

FIG. 5 is a flow chart showing a process of normalizing the electrophoregram according to the invention;

FIG. 6 illustrates the electrophoregram for explaining a method of detecting two reference points;

FIGS. 8A, 8B, 9, 10, 11A, 11B and 11C show some examples of electrophoregrams displayed together with a standard electrophoregram or a normal range;

FIGS. 14, 15 and 16 show parts of electrophoregrams including specific shapes;

FIG. 17 is a flow chart of a process of detecting $\beta$-$\gamma$ bridging according to the invention;

DESCRIPTION OF THE PREFERRED EMBODIMENTS

Figure 1:
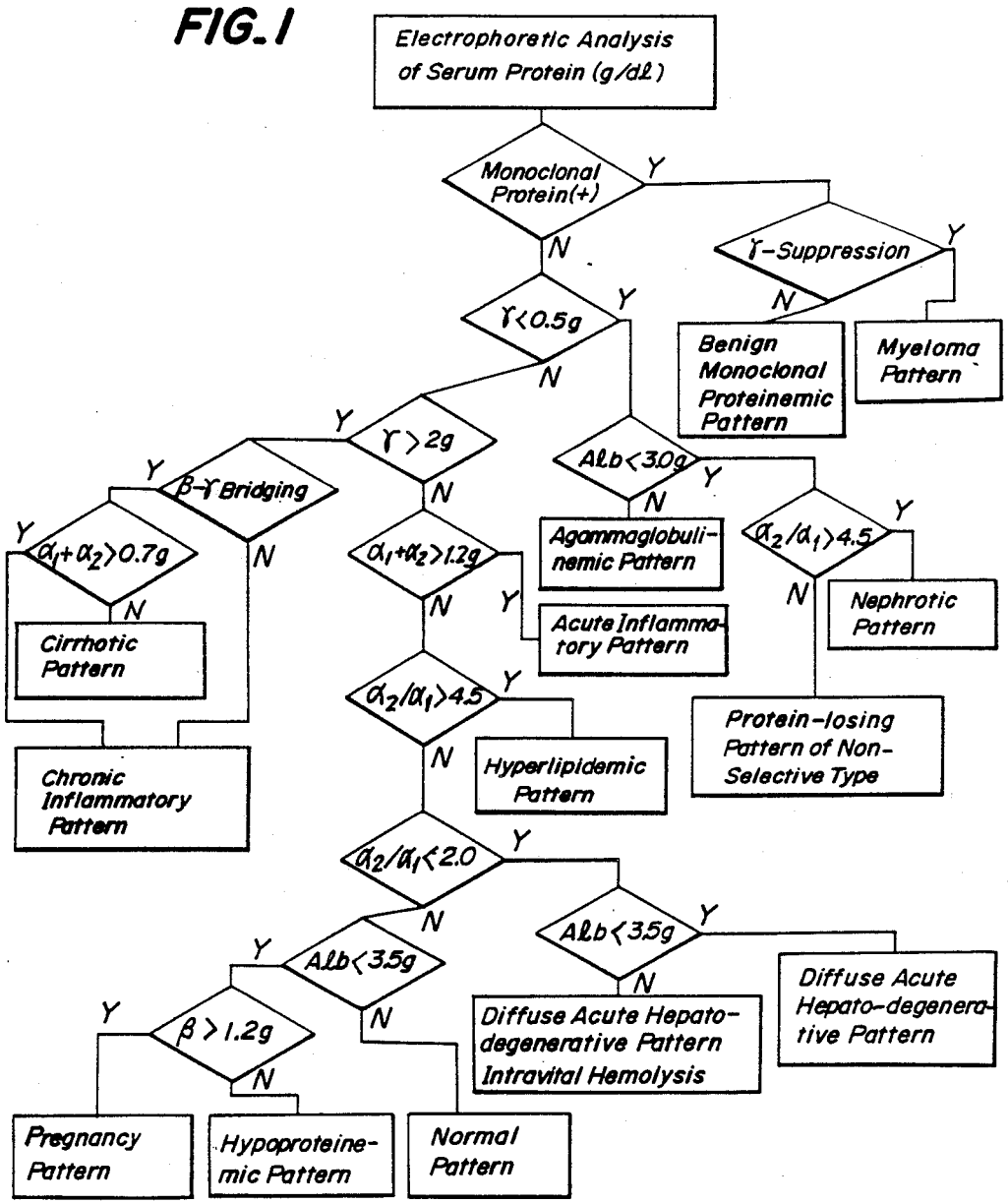
FIG. 1 is a flow chart showing a known method of deriving analytical results from an electrophoregram.

FIG. 2 is a schematic view showing a principal construction of the densitometer of electrophoretic apparatus for photoelectrically scanning an electrophoretic image. A substrate 1 which has been previously dyed, decolored and dried is fed by feeding rollers 2 into a photometering section 4 containing decalin 3 for making the substrate 1 transparent. The substrate 1 is photometered by the photometer device 5 and then is discharged by means of discharge rollers 6. The photometer device 5 comprises a light source 5a for emitting a light beam and a light receiving element 5b for receiving a light beam transmitted through the substrate 1. The photometer device 5 is moved at a constant speed of, for instance, 8 mm/sec in a scanning direction b perpendicular to a feeding direction a of the substrate 1 as illustrated in FIG. 3. In this manner electrophoretic images 7 of various components formed on the substrate 1 are photoelectrically scanned to produce an electrophoretic image signal.

The electrophoretic image signal thus obtained by scanning the electrophoretic images in the densitometer is sampled at a suitable sampling period to derive a series of digital data samples. Various measured values of test items e.g. fraction percentages are calculated from the data samples thus obtained and these values are printed on a test report by a printer. On the test report, an electrophoregram is also recorded. In case of a serum sample of a human being, an electrophoregram recorded on the test report includes fractions of pre-albumin, albumin, $\alpha_1$-globulin, $\alpha_2$-globulin, $\beta$-globulin and $\gamma$-globulin, these fractions being successively recorded in the order mentioned above.

FIG. 4 is a block diagram illustrating an embodiment of an apparatus for carrying out the method according to the invention. In the present embodiment, various kinds of proteins contained in serum samples of human beings are to be analyzed. One or more sets of electrophoretic images of one or more serum samples are formed on a substrate 1 and are photoelectrically scanned by a densitometer comprising a light source 5a and a light receiving element 5b. The construction of the densitometer itself is the same as that of the known densitometer. The light source 5a and light receiving element 5b are moved in a scanning direction relative to the substrate 1 at a constant speed, e.g. 8 mm/sec. An output photoelectrically converted signal from the light receiving element 5b is amplified by a log-amplifier 12 and is converted into a signal representing an optical absorbance of electrophoretic images, i.e. fraction images of various kinds of proteins. Therefore, this signal is also called an electrophoretic image signal. Then, the converted electrophoretic image signal is sampled and converted into digital data samples by an A/D converter 13 in synchronism with clock pulses having a repetition period corresponding to a sampling period which may be determined in accordance with analytic conditions such as electrophoretic time period. In the present embodiment, the sampling period is set to 12 m·sec, while the electrophoretic time is set to 40 minutes. The digital data samples thus obtained are supplied to a memory 15 and are stored therein under the control of a central processing unit (CPU) 14. The apparatus further comprises a keyboard 16 and a cathode ray tube (CRT) 17 for entering and monitoring various commands, data and images, floppy disc 18 and a printer 19.

In the present embodiment, after the data samples stored in the memory 15 have been subjected to the smoothing treatment and the auto-zero treatment for removing any fluctuation of a base line due to a variation in an intensity of light, the data samples are further subjected to a normalizing process. Then fraction percentages, and A/G ratio are calculated and displayed on the CRT 17 together with a densitogram. These results are recorded on a test report 20 by means of the printer 19. The data is also stored in the floppy disc 18.

FIG. 5 is a flow chart showing an embodiment of the normalization process according to the invention. In the present embodiment, an electrophoregram having a given electrophoretic expansion length is represented by 350 data samples, and a peak point of an albumin fraction is made coincident with a hundredth point and a peak point of the β-globulin fraction is set at a two hundredth point. It should be noted that the albumin fraction has a large peak and the β-globulin fraction has a stable peak, so that these peak points can be preferably selected as the reference points for the normalization. It should be further noted that the number of data samples obtained by A/D-converting the electrophoretic image signal is larger than 350.

In the normalizing process, at first the reference points, i.e. the peak points of the albumin and β-globulin fractions are detected from the data samples stored in the memory 15. Now several methods of detecting the reference points will be explained.

FIRST METHOD OF DETECTING REFERENCE POINTS

The data samples are compared with a threshold level to extract a series of data samples which exceed the threshold level as shown in FIG. 6. Said threshold level has been determined such that both extreme points of the extracted series of data samples are substantially made coincident with extreme points of the electrophoretic expansion length. Then peaks are detected in ranges $l_1$ and $l_2$, respectively, the ranges $l_1$ and $L_2$ being predetermined on the basis of the left and right hand points of the extracted series of data samples, respectively. One peak having the heighest concentration in the range $l_1$ is then assumed to be the peak of albumin fraction and a peak detected in the range $l_2$ is determined as the peak of β-globulin fraction. In this manner, the reference points on the electrophoregram can be detected.

SECOND METHOD OF DETECTING REFERENCE POINTS

A series of data samples are successively accumulated from both end points of the series and when accumulated values reach predetermined values, respectively, relevant sample positions are determined as extreme points of the densitogram. Then, the peaks of albumin and β-globulin fractions are detected in the ranges $l_1$ and $l_2$ in the same manner as that of the first method. For instance, when an accumulated value of data samples from the left hand end i.e. from a positive polarity side to the albumin fraction becomes equal to two percentages of a total accumulation value and when an accumulated value from the right hand end, i.e. from a negative polarity side of γ- globulin image becomes equal to one percentage of the total accumulation value, it is possible to extract data sample which represent the electrophoretic image which substantially corresponds to the electrophoretic expansion length obtained by the inspection with naked eyes.

THIRD METHOD OF DETECTING REFERENCE POINTS

On the substrate a normal or standard serum sample is also applied to form a standard electrophoretic image of the normal sample. Then the standard electrophoretic image is scanned to derive a series of standard data samples. Then a peak position of albumin fraction of the standard sample is detected and thereafter a peak position of β-globulin is detected as a third peak counted from the albumin peak toward the negative polarity side. Next, a peak point of albumin fraction of a test sample is detected and then a peak point of β-globulin fraction is detected by detecting a peak near a position which is shifted toward the negative polarity side by a distance which is equal to a distance between the albumin peak and the β-globulin peak of the standard sample. In this method, the peak point of albumin fraction can be detected by comparing the data samples with a threshold level having a relatively large amplitude, because the albumin peak has a remarkably large height. Further, the peak of albumin fraction may be detected by the method disclosed in U.S. Pat. No. 4,666,577. In this method, at first the largest peak value $D_M$ is detected among all the data samples, and then a first peak which exceeds a threshold level having a sixteenth of $D_M$ is detected as the albumin peak from the positive polarity side. It should be noted that the threshold level $D_M/16$ is experimentally determined such that a peak of prealbumin fraction can be surely ignored, and even if $D_M$ is not the albumin peak, the albumin peak can be detected positively. It is also possible to use a threshold value which is not equal to $D_M/16$.

In the manner explained above, it is possible to detect the peak position of albumin fraction which has usually a remarkable high value and the peak position of β-globulin fraction whose position in the electrophoretic image is very stable.

NORMALIZATION OF X-AXIS

In a next step II, the data samples are normalized on the X-axis such that the albumin peak and β-globulin peak are made coincident with predetermined points on the electrophoregram, e.g. the hundredth data point and the two hundredth data point, respectively. For instance, when the detected albumin peak and β-globulin peak of the serum sample are on a hundred twentieth (120th) point and a two hundred thirtieth (230th) point, respectively, a distance between these points is equal to $230-120=110$. Then the data samples are shifted on the X-axis in accordance with a ratio of said distance 110 to a standard distance of 100 ($=200-100$) and the albumin and β-globulin peaks are made coincident with the 100th and 200th points, respectively. If one or more data samples corresponding to data points on the X-axis are not existent in the detected data samples of the test sample, data samples have to be formed by interpolation.

In this manner, the normalization on the X-axis is performed. Then, the number of data samples is made equal to the standard value of 350 and the albumin peak and β-globulin peak are set at the predetermined positions of 100th and 200th points, respectively.

NORMALIZATION ON Y-AXIS

Next, in a step III, the normalization on the Y-axis is carried out in accordance with the ratio of the number of data samples of the test sample between the two reference points to the number of samples between the two predetermined points on the X-axis. In the above example, the ratio is equal to 110/100. That is to say values of 350 data samples are multiplied by the ratio of 110/100. Then an accumulated value of the 350 normalized samples is made substantially equal to an accumulated value of non-normalized samples of the test sample between corresponding peak points. That is to say, in the above example, each of 350 data samples is multiplied by 110/100 to effect the normalization on the Y-axis.

The above processes are carried out by reading the data samples out of the memory 15 under the control of the CPU 14, and normalized data samples are stored in the floppy disc 18.

NORMALIZATION OF CONCENTRATION

In a next step IV, the normalization of concentration is performed by relating accumulation values of respective fraction images to absolute concentration values of respective proteins in the test sample. To this end, a total amount of the proteins or an amount of albumin is measured by a chemical analyzer separately provided from the electrophoretic apparatus, and the thus measured amount is entered by means of the keyboard 16 or directly from the analyzer or an inspection computer system coupled with the analyzer on an on-line or off-line mode. The thus entered data is stored in the floppy disc 18. At the same time, a reference accumulation value for a unit density (1 g/dl) of the measured absolute concentration value is also stored in the floppy disc 18. For instance, when the concentration value of albumin is entered, the reference accumulation value for unit concentration (1 g/dl) of albumin is set to, for example 15,000 (A/D converted value). Then, if the concentration of albumin of 4 g/dl is entered, at first an accumulation value of albumin fraction is calculated in accordance with the normalized data samples and then a ratio of the thus calculated value to the reference accumulation value corresponding to the concentration of albumin is derived. For instance, if the accumulation value of the normalized albumin fraction is equal to 80,000 (A/D converted value), the reference accumulation value becomes equal to 4 (g/dl)×15,000=60,000. Then, the ratio of 60,000/80,000=0.75 is calculated. The normalization for concentration is then performed by multiplying respective values of the data samples by said ratio of 0.75. During this normalization for concentration, it is also possible to correct variation in color between the fraction images. Further, in case of entering the total amount of proteins, the ratio may be similarly derived by dividing the reference accumulation value corresponding to the entered total amount by the accumulation value of all the fractions.

In the manner explained above, the normalization on the X-axis, normalization on the Y-axis and normalization for concentration are effected successively and the normalized data samples are stored in the floppy disc 18.

In the present embodiment, the data samples of the electrophoregram of test sample are subjected to the normalization on the X-axis, the normalization on the Y-axis and the normalization for concentration on the basis of the entered amount of a single protein or the entered total amount of proteins. Therefore, even if amounts of test samples applied on substrates vary from each other and electrophoretic expansion lengths of electrophoregrams of test samples fluctuate, the electrophoregrams formed by the normalized data samples have the same electrophoretic expansion length and fraction percentages of various proteins represent absolute concentrations of proteins in an accurate manner. Therefore, it is possible to obtain the normalized electrophoregram representing accurately the concentrations of respective fraction images, so that difference in electrophoretic mobility, existence of M-protein, and existence of specific waveforms or shapes can be detected accurately and can provide useful information for diagnosing diseases precisely. Further, since the reference points of electrophoregrams of respective test samples are made identical with each other, it is possible to effect the accurate comparison between the electrophoregrams in an easy manner.

It should be noted that it is sufficient to effect only the normalization on the X-axis or the normalizations on the X- and Y-axes. Further the normalization for concentration may be carried out prior to the normalization on the X-axis. Moreover, the reference points may be set to points other than the peak points of albumin and β-globulin fractions. For instance, peak points of other protein substances or end points of the electrophoretic image may be selected as the reference points.

In order to analyze electrophoregrams to provide useful information for diagnosing diseases accurately, it is preferable to compare an electrophoregram of respective test samples with a standard electrophoregram of normal sample. In the present embodiment, the standard electrophoregram is displayed or printed on the same display area or the same printing area as the electrophoregram of test sample. This will be explained hereinbelow.

Figure 7:
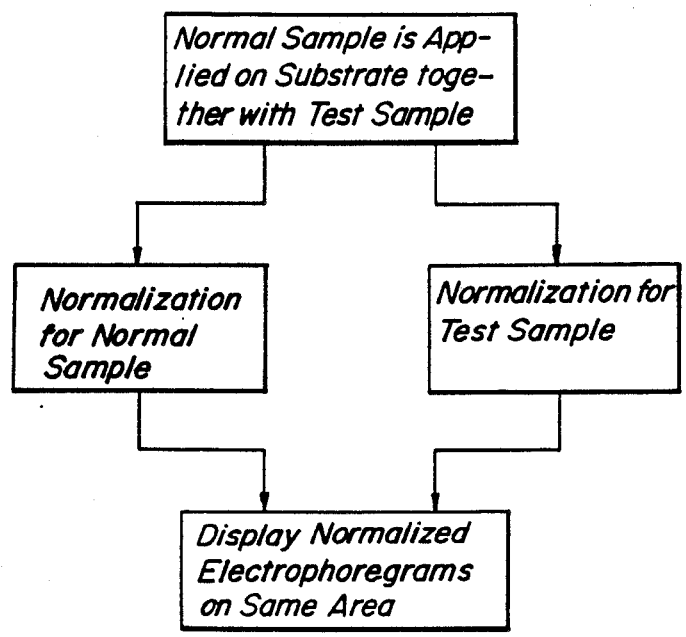
FIG. 7 is a flow chart representing a manner of displaying normalized electrophoregrams according to the invention.

FIG. 7 is a flow chart showing a general process for displaying the electrophoregram of test sample and normal sample in a superimposed manner. At first, at least one normal sample is applied on a substrate together with test samples and the substrate is subjected to electrophoresis to obtain a standard electrophoretic image of the normal sample and electrophoretic patterns of the test samples. Then these electrophoretic images are photoelectrically scanned to derive data samples, and then data samples of the normal sample are subjected to the normalization to derive a series of normalized data samples relating to a standard electrophoregram and at the same time the data samples of test sample are subjected to the normalizing process to obtain a series of normalized data samples relating to a normalized electrophoregram of test samples. Then, these electrophoregrams are displayed on the same display area of the CRT 17 in a superimposed manner. At the same time these electrophoregrams of test sample and normal sample are printed on the same area of the test report 20 by means of the printer 19 in a superimposed manner.

Now several embodiments of the method of displaying the electrophoregrams in a superimposed manner will be explained.

Figure 8A:
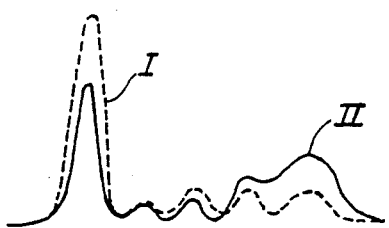
Figure 8B:
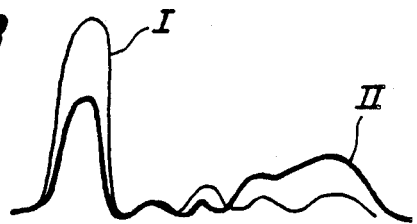
Figure 9:
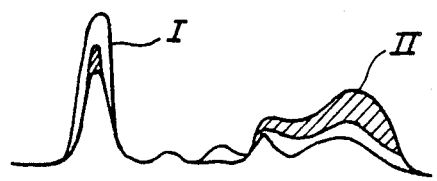

In an embodiment illustrated in FIG. 8A, a standard electrophoregram I of normal sample is displayed by a broken line, while an electrophoregram II of test sample is displayed by a solid line. In an embodiment shown in FIG. 8B, the standard electrophoregram I is displayed by a thin solid line, while the electrophoregram II of test sample is displayed by a thick solid line. These electrophoregrams I and II may be displayed by lines having different colors or different densities or brightness. Further a normal range is calculated from the data samples of standard electrophoregram of normal sample and then the data samples of the electrophoregram of test sample are compared with the normal range. Then a portion of the electrophoregram of test sample which is out of the normal range may be displayed by a hatching as illustrated in FIG. 9. In this case, the hatching may be displayed by one or more colors different from the electrophoregrams. Moreover, said portion of electrophoregram out of the normal range may be also displayed by different color, thickness or brightness than the electrophoregrams.

Figure 10:
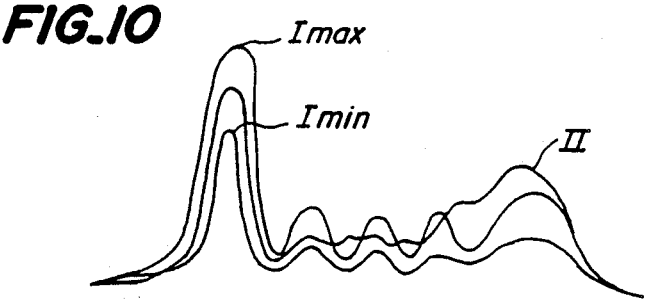

Further, as illustrated in FIG. 10, patterns $I_{max}$ and $I_{min}$ representing upper and lower limits of the normal range are displayed instead of the standard electrophoregram of normal sample. In this case regions of the electrophoregram of test sample above the upper limit and underneath the lower limit may be clearly distinguished from the normal range by different color or hatchings. Further, regions to be specially inspected or a dangerous region may be derived from the comparison with the standard electrophoregram and these regions may be displayed by hatching or different colors.

In the above embodiment, the standard electrophoregram of normal sample and/or the normal range derived from the standard electrophoregram are displayed on the CRT 17 and are printed on the test report 20. According to the invention, it is also possible to use test reports on which patterns relating to the standard electrophoregram of normal sample have been previously printed. FIGS. 11A to 11C show several embodiments of such test reports. In the embodiment illustrated in FIG. 11A, a standard electrophoregram III has been printed on a test report 21 by a broken line. In the embodiment of FIG. 11B, the standard electrophoregram III has been printed by a solid line, and in the embodiment depicted in FIG. 11C, upper and lower limit patterns $III_{max}$ and $III_{min}$ have been previously printed on the test report 21. It should be noted that a length of these patterns has to be made equal to the electrophoretic expansion length of normalized electrophoregrams of test samples. Further in case of using the above test reports having the patterns relating to the standard electrophoregram previously printed thereon, it is not always necessary to derive the standard electrophoregram of normal sample. However, it is preferable to derive the standard electrophoregram of normal sample, because in such a case the standard electrophoregram may be advantageously used for the normalization and the judgment of diseases.

According to further aspect of the present invention, it is possible to analyze the electrophoregram to provide for doctors a lot of useful data or information for diagnosing patients. To this end, according to the invention it is necessary to detect specific waveforms or shapes of the normalized electrophoregram. Now several methods of detecting specific waveforms will be explained.

One of the most important specific configuration of the electrophoregram is an M-protein peak. The M-protein peak may appear at any point on the electrophoregram, but usually the M-protein peak appears between the $\beta$-globulin fraction and the $\gamma$-globulin fraction. It should be noted that the M-protein peak is produced by monoclonal proteins contained in the test serum sample, and thus the M-protein peak appears as a monoclonal spike having a narrow width. The M-protein may be classified in to benign M-protein and malignant M-protein. The benign M-protein appears as a spike which is superimposed on a usual electrophoregram, but in the malignant M-protein one or more protein substances in the electrophoregram are suppressed specifically.

Figure 12A:
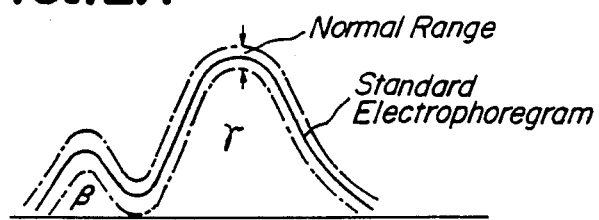
FIGS. 12A, 12B and 12C illustrate a few examples of the electrophoregram having specific pattern configurations.
Figure 12B:
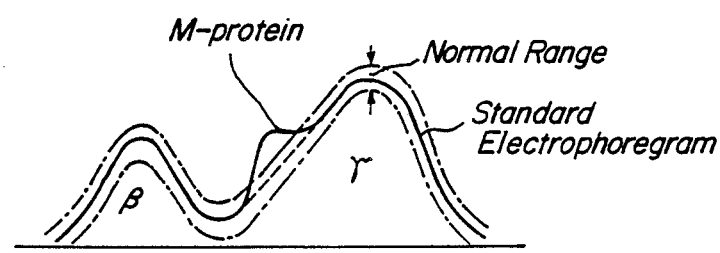
Figure 12C:
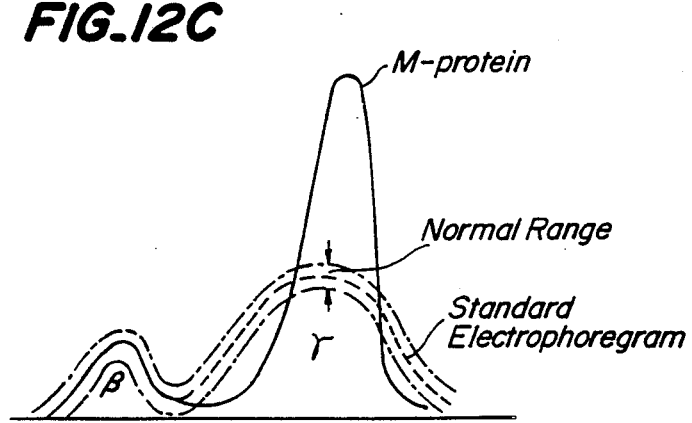

Owing to the above mentioned specific properties of the M-protein, it is possible to detect the M-protein peak by judging whether or not a sharp peak is existent between the $\beta$-globulin fraction and the $\gamma$-globulin fraction. As shown in FIG. 12A, when an electrophoregram does not include the M-protein peak between the $\beta$-fraction and the $\gamma$-fraction, there are smooth valleys and smooth peaks. When a test sample contains benign M-protein, there is found an additional peak between the $\beta$-fraction and the $\gamma$-fraction as illustrated in FIG. 12B, so that the electrophoregram has a rather complicated shape or configuration. If a test sample includes the malignant M-protein, there appears a sharp peak as shown in FIG. 12C. Further, in this case, the $\gamma$-fraction is suppressed on both sides of the M-protein peak.

In order to detect merely the M-protein peak, it is sufficient to detect whether or not a peak is existent between the $\beta$-fraction and the $\gamma$-fraction, e.g. between 200th data point and 300th data point. However, such a detection method could not judge whether the detected M-protein peak is benign or malignant. Therefore, it is necessary to detect whether the $\gamma$-fraction is suppressed or not near the detected M-protein peak.

Figure 13:
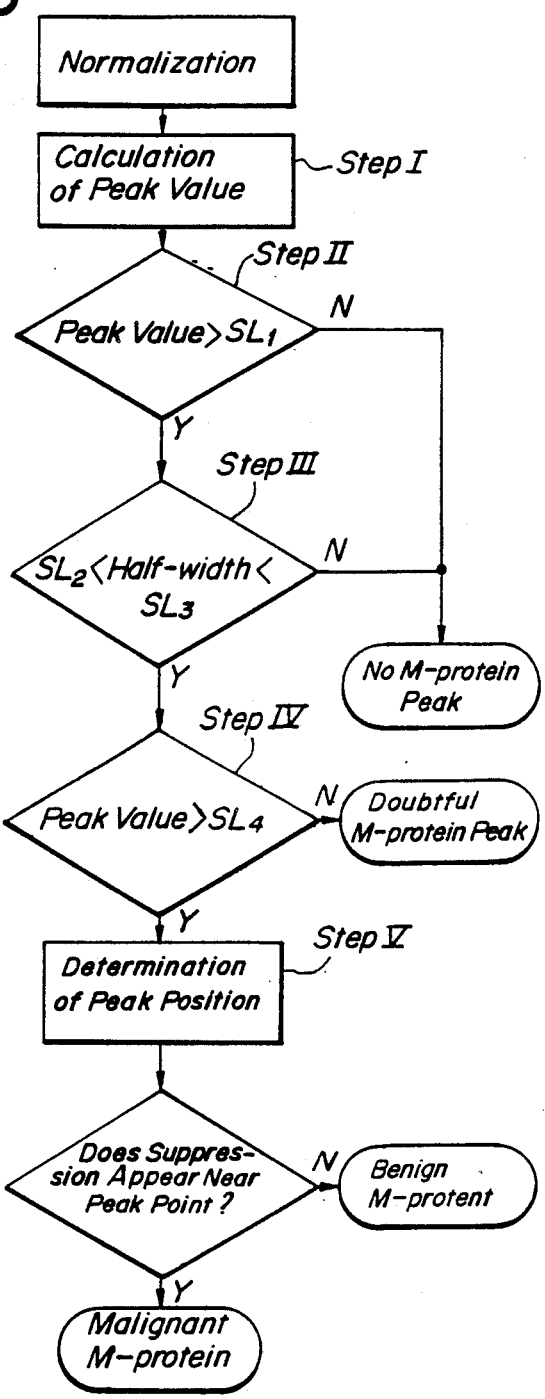
FIG. 13 is a flow chart showing a process for detecting the M-protein according to the invention.

Now the method of detecting and processing the M-protein between the $\beta$-fraction and the $\gamma$-fraction will be explained with reference to a flow chart shown in FIG. 13. After the data samples of the electrophoregram of test sample have been normalized as explained above, in a first step I, a degree of a peak hereinafter referred to peak value is detected within a predetermined range corresponding to the distance between the $\beta$-fraction and the $\gamma$-fraction. Now several methods of calculating the peak value will be explained.

FIRST METHOD OF CALCULATING PEAK VALUE

At first a detection range having a width 2k is set on both sides of a data point i as illustrated in FIG. 14. It is assumed that data values at points $i-k$, $i$ and $i+k$ have $D_{i-k}$, $D_i$ and $D_{i+k}$, respectively. Then an area S of a portion surrounded by the electrophoregram and a straight line connecting the data value $D_{i-k}$ and $D_{i+k}$ is calculated. In case of adopting the trapezoidal integration, said area S can be calculated by the following equation.

$$S = \left( \frac{1}{2} D_{i-k} + D_{i-(k-1)} \ldots + D_{i-1} + D_i + D_{i+1} + \ldots + D_{i+(k-1)} + \frac{1}{2} D_{i+k} \right) - (D_{i-k} + D_{i+k})/2 \times 2k$$

It is matter of course that the area S may be calculated by other methods than the trapezoidal integration. For instance, Simpson's rule may be utilized.

The inventor has confirmed experimentally that the value of k may be advantageously set to 3 to 6. If k is set smaller than 3, although it is possible to detect the fine variation, the area S is affected by small noise. Contary to this, if k is set larger than 6, although the influence of noise can be reduced due to the smoothing effect, the fine variation could not be detected. The value of k will be equally used in other methods which will be explained later.

By judging the area S thus calculated, it is possible to detect not only a definite M-protein peak, but also a small M-protein peak as shown in FIG. 15.

SECOND METHOD OF CALCULATING M-PROTEIN PEAK

At first the area S is calculated in the manner explained above. Then a value of S/2k is calculated. This value of S/2k represents an average height within the range having the width of 2k. Therefore, the dependency of S/2k upon the detection width 2k becomes smaller than that of S. That is to say, if the detection width 2k is varied, the area S is changed accordingly, but the ratio S/2k is varied only slightly. Therefore, the ratio S/2k represents the degree of protrusion of M-protein peak much more faithfully.

THIRD METHOD OF CALCULATING M-PROTEIN PEAK

In this method, the degree of the protrusion of the M-protein peak is represented by $S/(2k)^2$. This value is a ratio of S/2k to the detection width 2k, and thus represents the degree of protrusion for a unit detection width. Therefore, if protrusions have analogous shapes, the values $S/(2k)^2$ becomes identical width each other. In this case, the detection width 2k determines the degree of the smoothing.

FOURTH METHOD OF CALCULATING M-PROTEIN PEAK

In this example, the degree of protrusion is calculated by the second derivative. In this case, it is necessary to express the electrophoregram by a suitable function. This may be performed by, for instance, the least squares method. Then a second derivative of an approximate function thus obtained is calculated to derive the peak value. Now several examples of second derivatives $F''(i)$ are shown for different detection widths of 5, 7 and 9 data points, respectively. In these examples, the electrophoregram is represented by an approximate function of a parabolic equation, $y=ax^2+bx+c$. In case of 5 data points (2k=4), $F''(i)=(2D_{i-2}-D_{i-1}-2D_i-D_{i+1}+2D_{i+2})/7$. In case of 7 data points (2k=6), $F''(i)=(5D_{i-3}-3D_{i-1}-4D_i-3D_{i+1}+5D_{i+3})/42$. In case of 9 data points (2k=8), $F''(i)=(28D_{i-4}+7D_{i-3}-8D_{i-2}-17D_{i-1}-20D_i-17D_{i+1}-8D_{i+2}+7D_{i+3}+28D_{i+4})/462$. The peak value thus calculated does not inherently depend upon the detection width 2k. Therefore, the detection width 2k determines merely the smoothing.

After the peak value representing the degree of protrusion has been calculated by one of the above explained methods, in a second step II, it is judged whether the peak value is larger than a predetermined threshold value $LL_1$. If the peak value is equal to or smaller than $SL_1$, it is judged that there is no M-protein peak. Contrary to this, if the peak value is larger than $SL_1$, a next step III is performed. In this step III, a half-width of the detected peak is calculated and then the calculated half-width is compared with upper and lower limits $SL_2$ and $SL_3$. If the half-width is out of a range between $SL_2$ and $SL_3$, it is judged that there is no M-protein peak. If the half-width is within said range, a next step IV is carried out. In this step IV, the peak value is compared with another threshold value $SL_4$ which is larger than $SL_1$. As a result of this comparison, if the peak value is equal to or smaller than $SL_4$, it is judged there is a possibility that the relevant electrophoregram might include the M-protein peak. If the peak value is larger than $SL_4$, there is judged that a definite M-protein peak is existent. In the later case, a next step V is further performed. In this step V, a data position of the peak is detected.

The inventor has conducted various experiments in which the electrophoregrams were normalized in such a manner that the accumulation value was equal to 100,000 for a total amount of proteins of 7 g/dl. Then the peak values were calculated by the second method, while the value k was changed to 3 to 6 and 10 to 30. It has been confirmed that M-protein peaks having substantially independent peaks were detected, while $k=3\sim6$ and the peak value of S/2k was larger than 30. For $k=10\sim30$, very small M-protein peaks having no definite peaks were detected. By setting the half-width to a range of 10 to 20 data points, it was possible to separate positively M-protein peaks from $\beta_{1C}$ peaks or fibrinogen peaks (in case of blood plasma; half-width is smaller than 10 data points) which peaks appear near the valley between the $\beta$-fraction and the $\gamma$-fraction.

Ater the data point of the M-protein peak has been detected, in a step VI sample values of data points near the detected peak point are compared with the normal range calculated from the standard electrophoregram to determine whether or not the data samples are smaller than the normal range. Upon this comparison, if there are one or more samples which are below the normal range, it is determined that there is the $\gamma$-suppression. Then, it can be judged that the detected M-protein peak is malignant (myeloma). Contrary to this if the data samples are in the normal range, the M-protein is judged to be benign. The normal range may be set to ±25% of data samples of the standard electrophoregram. It should be noted that the data samples for representing the normal range may be previously stored in the memory 15 or floppy disc 18 and a necessary part of the data samples may be extracted therefrom.

Next a method of processing the $\beta$-$\gamma$ bridging or $\beta$-$\gamma$ linking will be explained. The $\beta$-$\gamma$ bridging is a phenomenon in which the $\beta$-fraction could not be clearly separated from the $\gamma$-fraction due to the fact that the valley between the $\beta$-fraction and $\gamma$-fraction is filled with an increased amount of polyclonal $\gamma$-fraction (IgG, IgM, IgA). When the $\beta$-$\gamma$ bridging appears remarkably, the peaks of $\beta$- and $\gamma$-fractions are connected by a smooth line and definite fraction point could not be detected between these fractions. In the known electrophoregram, if the $\beta$-fraction deceases, a pseudo $\beta$-$\gamma$ bridging appears although the $\gamma$-fraction is normal. Therefore, in order to distinguish a pseudo $\beta$-$\gamma$ bridging from the real $\beta$-$\gamma$ bridging it is necessary to check concentrations of fractions (g/dl). In the present embodiment, it is possible to distinguish the pseudo and real $\beta$-$\gamma$ bridgings from one another by a process illustrated in FIG. 17. At first, a series of data samples is normalized to derive a series of normalized data samples relating to a normalized electrophoregram. Then, in a step I, peak points of $\beta$- and $\gamma$-fractions of the normalized electrophoregram of normal serum sample are detected. Next, in a step II, a portion of the normalized data samples of test sample is extracted in accordance with the detected peak points of $\beta$- and $\gamma$-fractions of normal sample. Then respective values of the thus extracted data samples are compared with respective values representing the normal range. In case of using no normal sample, peak points of the $\beta$- and γ-fractions of the normalized test sample are detected, then a portion of the normalized data samples between the peak points is extracted, and further the extracted data samples are compared with the values representing the normal range.

If no extracted data sample exceeds the normal range, it is judged that there is not the β-γ bridging. Contrary to this, if one or more extracted data samples exceed the normal range, then in a next step III, it is judged whether or not a width of a portion of the data samples exceeding the normal range, i.e. the number sampling points of the data samples exceeding the normal range is compared with a reference width. This is due to the fact that since the β-γ bridging shows a polyclonal increase, the width of a portion of data samples exceeding the normal range is wide. In case of the $\beta_{1C}$ of fibrinogen which usually appears near the valley between the β- and γ-fractions, the width of a portion of data samples which exceeds the normal range is much narrower than that of the β-γ bridging. Therefore, by comparing the width of a portion of data samples exceeding the normal range with the reference width, for example 60% of the width between the β- and γ-peak points, the β-γ bridging can be positively distinguished from the $\beta_{1C}$ and fibrinogen. If the detected width is equal to or narrower than the reference width, it is judged that there is no β-γ bridging. If the detected width is broader than the reference width, it is further confirmed in a step IV whether or not the M-protein peak is existent within the portion of data values exceeding the normal range by the steps I and II or steps I to IV of the process shown in FIG. 13. If the M-protein peak is detected, it is assumed that the relevant increase is due to the M-protein, and it is judged that no β-γ bridging is actually existent. On the contrary, if the M-protein peak is not detected, it is assumed that the relevant increase is due to the polyclonal increase and the β-γ bridging is judged to be actually existent.

It should be noted that if the M-protein peak is first detected and then the existence of the β-γ bridging is detected as shown in the flow chart of FIG. 1, the step IV illustrated in FIG. 17 may be deleted.

In the manner explained above, it is possible to detect accurately the β-γ bridging due to the polyclonal increase.

Next a manner of detecting the leading will be explained with reference to the albumin fraction.

Figure 18:
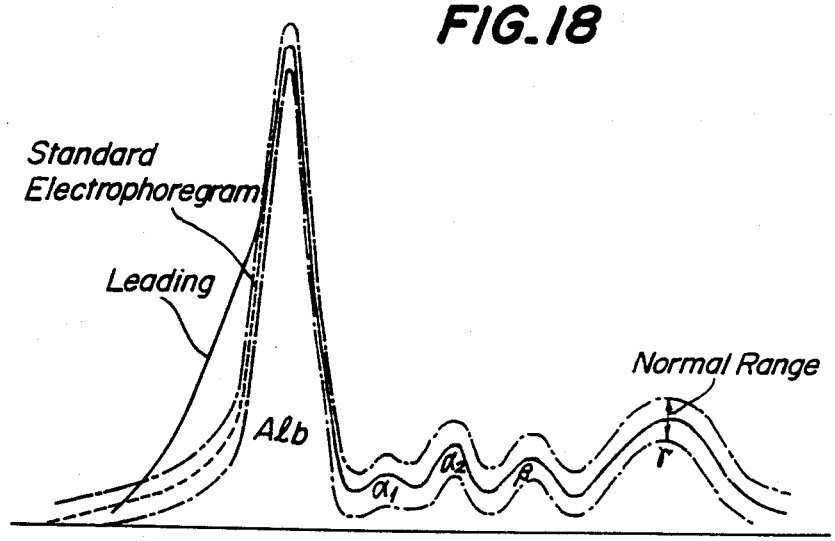
FIG. 18 represents an electrophoregram having a leading.

Usually the albumin fraction is formed by a single kind of protein and its fraction pattern is symmetrical with respect to its peak point. Further the electrophoretic mobility of albumin is very stable and the concentration of albumin is high. Due to the above features, the albumin fraction is the most remarkable pattern in the electrophoregram. However, in case of hyperjaundice serum, hyperlipid serum, antibiotic injection, etc. albumin is bound with bilirubin, free fatty acid and drugs, so that the electrophoretic mobility is changed. This results in that the albumin fraction shows a leading toward the positive polarity side of the electrophoregram and becomes asymmetrical as depicted in FIG. 18.

Figure 19:
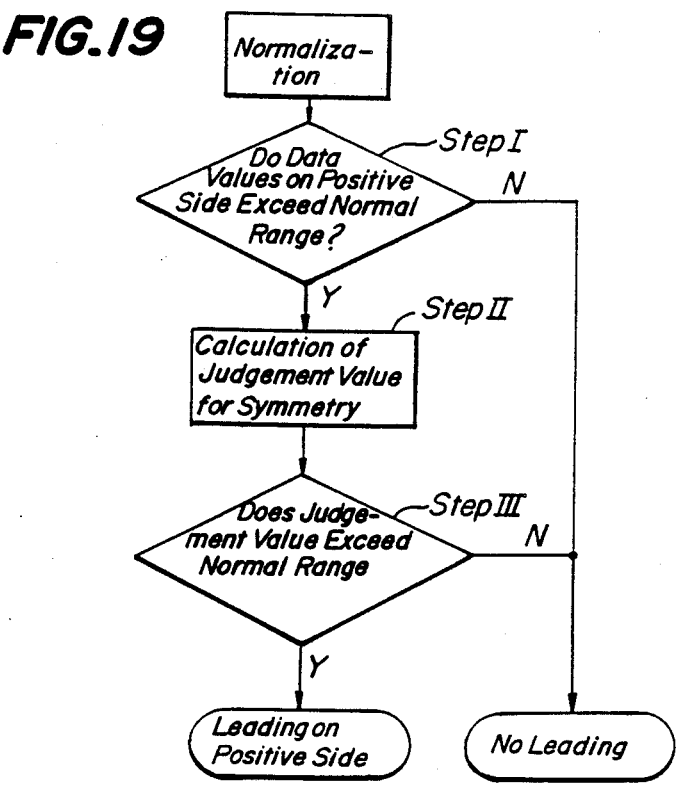
FIG. 19 is a flow chart depicting a manner of detecting the leading according to the invention.

In the present embodiment, the above mentioned leading of albumin fraction toward positive polarity side is detected by a process illustrated in FIG. 19. At first, in a step I, there is checked whether or not one or more sample values of the normalized data situating on the positive polarity side with respect to the albumin peak point exceed the normal range. If all the sample values on the positive polarity side with respect to the albumin peak do not exceed the normal range, it is judged that there is not the leading. On the contrary, if one or more data values exceed the normal range, then in a next step II there is calculated a judgment value which represents a degree of the symmetry of the albumin fraction in order to judge whether relevant increase is due to a general increase of albumin or due to the leading. Next, several examples of a method of calculating the judgment value will be explained.

FIRST CALCULATING METHOD

Figure 20A:
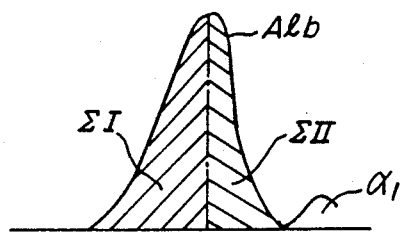
FIGS. 20A, 20B, 20C, 21A, 21B and 21C illustrate parts of electrophoregrams for explaining a method of detecting the symmetry according to the invention.

As illustrated in FIG. 20A, an accumulation value ΣI of sample values situating on the left-hand side, i.e. the positive polarity side with respect to the albumin peak and an accumulation value ΣII of sample values situating on the right-hand side, i.e. the negative polarity side with respect to the albumin peak are calculated and then a ratio of these accumulation values ΣI/ΣII is derived as the judgment value.

SECOND CALCULATING METHOD

Figure 20B:
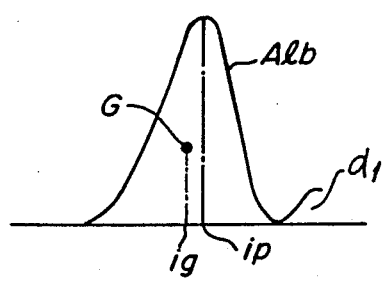

As depicted in FIG. 20B, a central moment point G of the albumin fraction is calculated and then a position $i_g$ of the point G is derived. This position $i_g$ may be generally calculated as a mean value position. Then a difference between the position $i_g$ and the peak position $i_p$ of the albumin fraction image ($i_p$-$i_g$) is derived as the judgment value.

THIRD CALCULATING METHOD

Figure 20C:
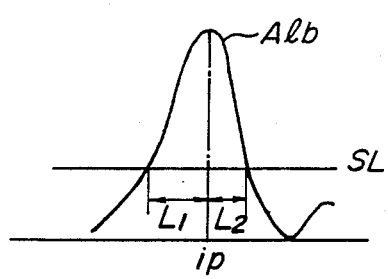

In this method, at first a suitable threshold level SL is set as shown in FIG. 20C. This threshold level SL may be a given fraction of the peak value of the albumin fraction. The sample values of the albumin fraction are compared with the threshold level and a portion of sample values which exceed the threshold level SL is detected. Next a width $L_1$ between the left-hand end of the detected portion and the peak position $l_p$ and a width $L_2$ between the right-hand end of the detected portion and the peak position $i_p$ are detected. Finally, a ratio $L_1/L_2$ is derived as the judgment value.

By means of one of the above calculating methods the judgment value is calculated, and then in a next step III (FIG. 19) the judgment value is compared with a normal range of judgment value which is calculated from the normalized data samples of normal sample. If the judgment value of test sample does not exceed the normal range, it is judged that there is no leading. On the contrary, if the judgment value exceeds the normal range, there is judged that the leading is existent on the positive polarity side of the albumin fraction.

In various judgment results such as M-protein, β-γ bridging and albumin leading are displayed on the CRT 17, and at the same time are printed on the test report 20 together with fraction percentages, A/G ratio, fraction concentrations and normalized electrophoregram.

Figure 21A:
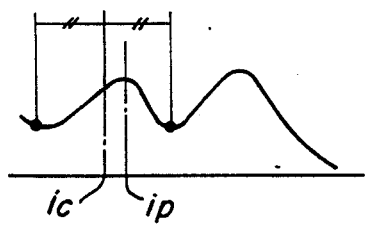
Figure 21B:
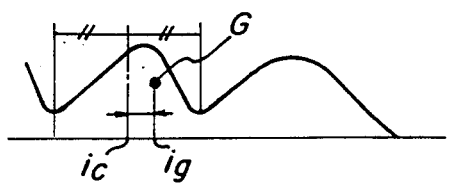
Figure 21C:
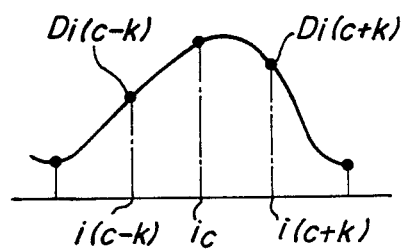

In the present embodiment, the leading on the positive polarity side with respect to the peak of the albumin fraction is detected. It is also possible to detect a leading on the negative polarity side of the albumin fraction by means of a similar method. For instance, a leading on the negative polarity side may be detected by detecting a portion of data values on the positive polarity side which are lower than the normal range and by checking whether or not a judgment value representing the symmetry exceeds a normal range. Further, the detection of existence of leading may be performed for other fractions than the albumin fraction. In such a case a judgment value estimating the degree of symmetry may be calculated not only by the above explained three methods, but also by detecting a deviation between the peak point $i_p$ and a middle point $i_c$ between adjacent fraction points as illustrated in FIG. 21A. The judgment value may also be derived by detecting a deviation between the peak point $i_p$ and position $i_g$ of the central moment point G as depicted in FIG. 21B. Further, the judgment value may be calculated by deriving a difference between data values $D_{i(c-k)}$ and $D_{i(c+k)}$ at positions which are separated from the center point $i_c$ of the fraction pattern by the same distance k or a difference between data values $D_{i(p-k)}$ and $D_{i(p+k)}$ at positions which are separated from the center point $i_p$ by the same distance k as shown in FIG. 21C. Further, a square of said difference or an accumulation of squares may be used as the judgment value. Moreover, a suitable corelative function may be used as the judgment value. It should be noted that the method of detecting and judging the M-protein appearing between the $\beta$- and $\gamma$-fractions, the suppression of $\gamma$-fraction due to the existence of the malignant M-protein, and $\beta$-$\gamma$ bridging may be equally applicable to the detection of change in amounts of proteins and minor peaks for other proteins such as albumin, $\alpha_1$- and $\alpha_2$-proteins. Moreover, it is not always necessary to determine fixedly the normal range as $\pm 25\%$ of the normal sample, but the normal range may be set for respective proteins or may be determined asymmetrically.

According to one aspect of the invention, the normalized electrophoregram of test sample is displayed and printed in superimposition with the normalized standard electrophoregram of normal sample, and at the same time a pattern obtained by comparing the above two electrophoregrams with each other is also displayed and printed besides the electrophoregrams in such a manner that respective measuring points of the pattern correspond accurately to respective measuring points of the electrophoregrams. Now a few examples of such a pattern will be explained.

(1) differences (DELTA$_i$) between the electrophoregrams of test sample and normal sample;

(2) a ratio (RATIO$_i$) of the electrophoregram of test sample to that of normal sample;

(3) a ratio (NRATIO$_i$) of the differences DELTA$_i$ mentioned in the first item (1) to a predetermined normal range.

In order to display the above mentioned three patterns, the following calculations are performed, while normalized concentrations values of test sample at respective measuring points i(i=1 to 350) are denoted as $D_i$, similar data values or normal sample $DS_i$, and values representing the normal range at respective measuring points are denoted as $NR_i$. Calculated values are stored in the memory 15 or floppy disc 18.

(1) DELTA$_i$=$D_i$−DS$_i$
(2) RATIO$_i$=$D_i$÷DS$_i$
(3) NRATIO$_i$=DELTA$_i$÷NR$_i$

In the present embodiment, the normal range NR$_i$ has been derived by processing statistically a lot of electrophoregrams and has been stored in the floppy disc 18 or ROM area in the memory 15.

Then, two electrophoregrams are printed in a superimposed manner on a predetermined area of the test report 20 by means of the printer 19 in accordance with the normalized data $D_i$ and DS$_i$ of test sample and normal sample. Then the test report 20 is fed by a predetermined amount and a pattern of DELTA$_i$ is printed with the same scale from the same position as those of the electrophoregrams. Next patterns of RATIO$_i$ and NRATIO$_i$ are printed in the same manner, while the test report 20 is intermittently fed by given lengths. In case of recording the patterns of RATIO$_i$ and NRATIO$_i$, a unit scale of concentration corresponds to concentration value 1,000, when the reference accumulation value for 1 g/dl of the total concentration value has been set to 15000 in the normalization process. Therefore, the measuring points of these patterns are aligned with the measuring points of the electrophoregrams.

Figure 22:
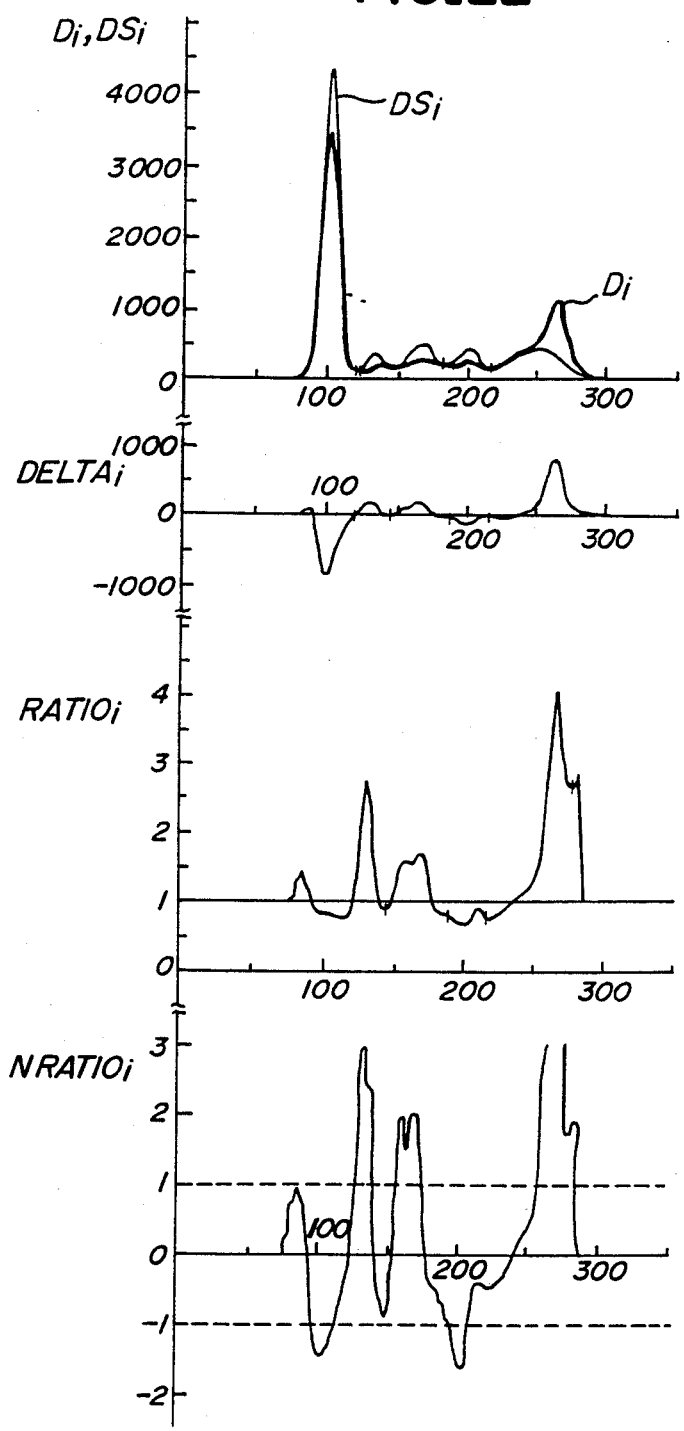
FIGS. 22 and 23 show some examples of patterns which are printed together with electrophoregrams.
Figure 23:
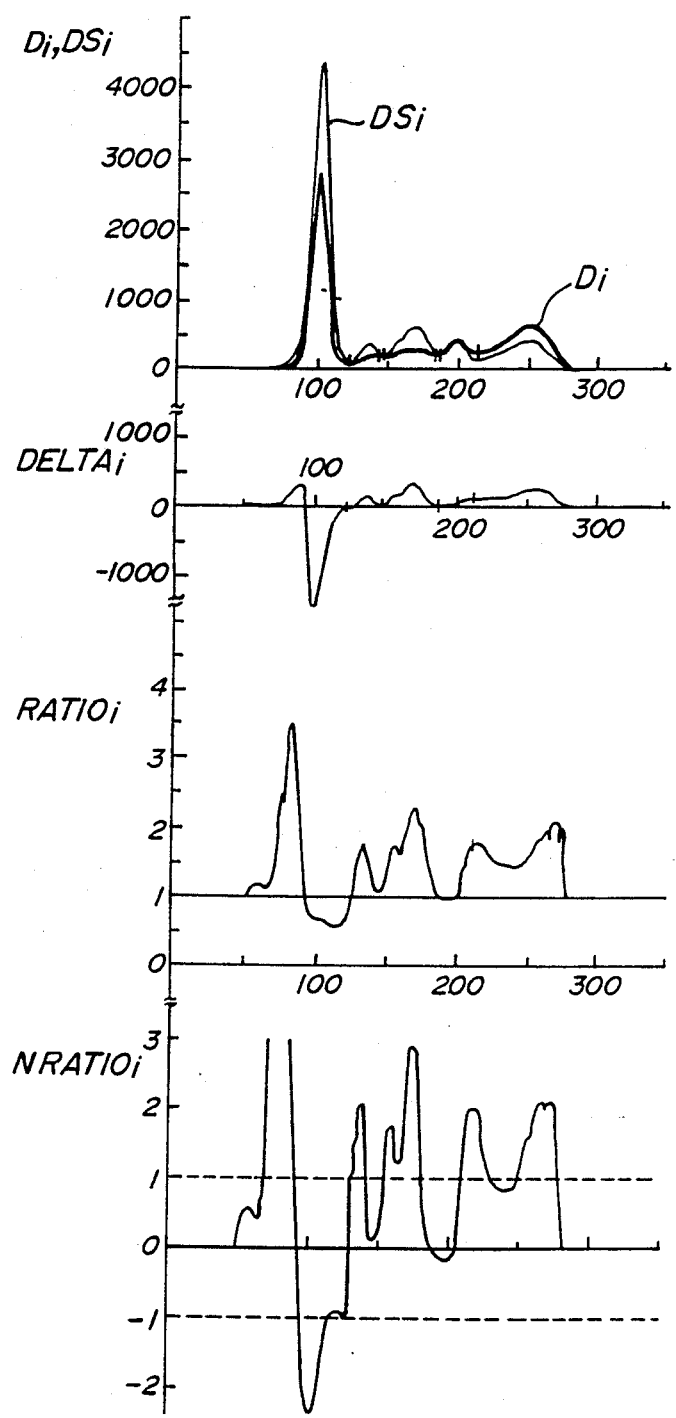

FIGS. 22 and 23 show two examples of the printed patterns. A thick curve denotes the electrophoregram $D_i$ of test sample and a thin curve represents the electrophoregram DS$_i$ of normal sample.

In the example shown in FIG. 22, the M-protein peak appearing on the $\gamma$-globulin fraction is expressed as a remarkable protrusion in the DELTA$_i$ pattern and is also represented as a great peak in the RATIO$_i$ pattern. Therefore, the M-protein peak can be clearly and easily detected from these patterns. Upon reading the patterns, since all the axes of abscissae have the same scale, the analysis and comparison of the patterns can be easily and accurately effected. Further a decrease in amount of albumin can be judged to be substantially identical with an absolute value of the M-protein peak from the pattern DELTA$_i$. Further, from the pattern RATIO$_i$ it can be judged that the ratio is relatively small due to the fact that the concentration of albumin is high and the change in albumin concentration is not so steep as the M-protein peak. In the pattern NRATIO$_i$, since the upper and lower limits of the normal range are denoted by broken lines of $\pm 1$, the deviation from the normal sample can be expressed clearly with the same weight. From the pattern NRATIO$_i$, the increase in $\alpha_1$-globulin and $\alpha_2$-globulin, the increase in the M-protein peak and an extent by which data values exceed the normal range can be easily estimated. It is further easily confirmed that the decrease in amount of albumin (DELTA$_i$) is very small.

In the example of the patterns illustrated in FIG. 23, an increase in IgA concentration which is specific to the $\beta$-$\gamma$ bridging appears as specific peaks near a fraction point between the $\beta$-globulin and $\gamma$-globulin in the patterns of RATIO$_i$ and NRATIO$_i$. Further, the leading on the negative polarity side of $\gamma$-fraction due to the polyclonal increase of $\gamma$-globulin appears as peaks in the patterns RATIO$_i$ and NRATIO$_i$ on the right-hand side of the $\beta$-$\gamma$ bridging. In this manner, the $\beta$-$\gamma$ bridging can be easily judged or detected from the patterns of RATIO$_i$ and NRATIO$_i$. In all the patterns of DELTA$_i$, RATIO$_i$ and NRATIO$_i$ remarkable peaks appear on the positive polarity side of the albumin fraction. From these peaks it can be easily judged that owing to the increase of bilirubin due to hepatic decease, the electrophoretic mobility of albumin is shifted toward the positive polarity side to produce the leading phenomenon. From the pattern of DELTA$_i$, increase in absolute value of $\alpha_1$-globulin, $\alpha_2$-globulin and $\gamma$-globulin can be easily determined, and from RATIO$_i$ and NRATIO$_i$ it can be easily judged that these increases are quite abnormal.

Figure 24A:
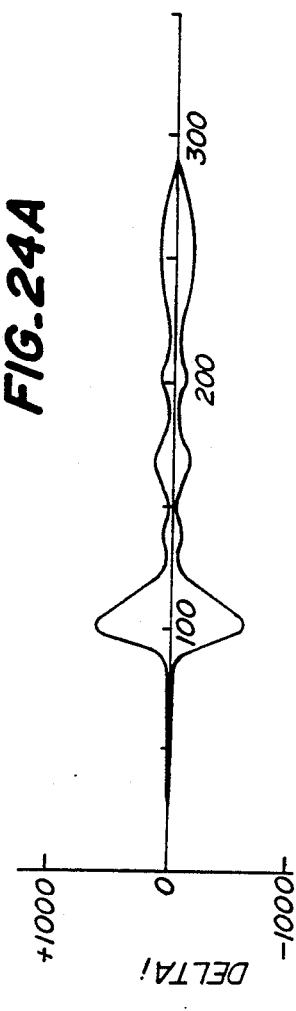
FIGS. 24A and 24B illustrate other examples of patterns printed on a test report.
Figure 24B:
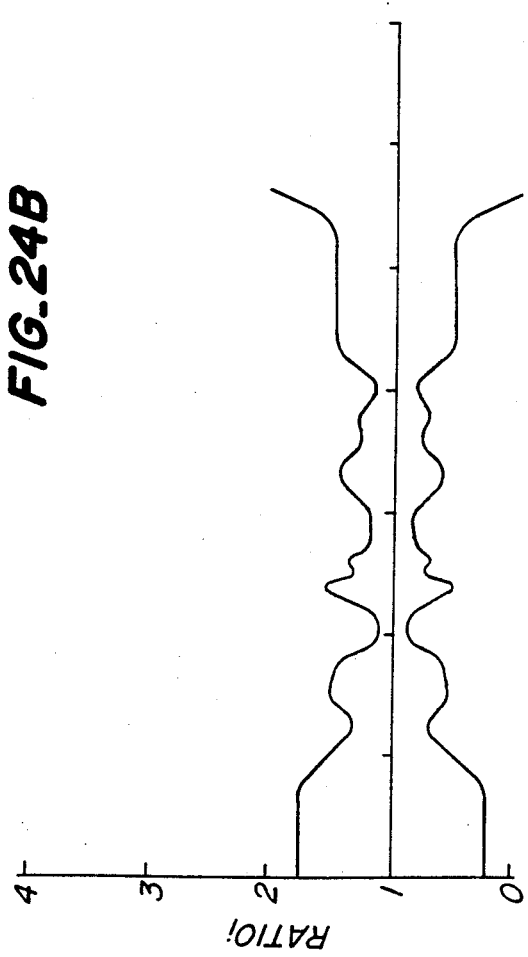

In a modified embodiment, the normal ranges of DELTA$_i$ and RATIO$_i$ have been previously printed on the test report as illustrated in FIGS. 24A and 24B. In such a case, actually calculated patterns DELTA$_i$ and RATIO$_i$ are printed in superimposed with the normal ranges. It should be noted that the normal ranges may be printed together with the patterns $DELTA_i$ and $RATIO_i$. Further portions of the patterns $DELTA_i$ and $RATIO_i$ which exceed the normal ranges may be printed in different color than other portions, or special marks may be added at these portions.

What is claimed is:

1. A method of producing a normalized electrophoregram, comprising the steps of:
   photoelectrically scanning an electrophoretic image of a test sample to derive an electrophoretic image signal;
   sampling the electrophoretic image signal to derive a number of data samples and storing said samples in a memory of a digital computer;
   referencing said stored data samples to detect at least two reference points on the electrophoretic image; and
   adjusting said stored data samples to make said reference points coincident with at least two predetermined points on an electrophoregram having a predetermined electrophoretic expansion length to produce a normalized electrophoregram.

2. A method according to claim 1 for processing a test sample, wherein said at least two reference points comprise two points set at peak points of albumin fraction and $\beta$-globulin fraction, respectively, said two points being related to two predetermined points on the electrophoregram.

3. A method according to claim 2, wherein said stored data samples are normalized such that a predetermined number of data samples exist between said two reference points.

4. A method according to claim 3, wherein said step of detecting the peak points of the albumin fraction and $\beta$-globulin fraction comprises
   determining end points of the electrophoregram by accumulating the stored data samples successively and by comparing an accumulated value with a predetermined threshold level;
   extracting a series of data samples within said end points;
   detecting one or more peak points of the extracted data samples within a predetermined range measured from one end of said series of extracted data samples;
   determining a peak point having the maximum value among the detected peak points as the peak point of the albumin fraction;
   detecting one or more peak points within a predetermined range set on the basis of the other end of said series of extracted data samples; and
   determining a peak point having the maximum value among the detected peak points as the peak point of the $\beta$-globulin fraction.

5. A method according to claim 3, wherein said step of detecting the peak points of the albumin fraction and $\beta$-globulin fraction comprises
   forming a standard electrophoretic image of a normal sample on the same substrate on which the electrophoretic image of the test sample is formed;
   scanning photoelectrically the standard electrophoretic image of normal sample to derive a standard electrophoretic image signal;
   sampling the standard electrophoretic image signal to derive standard data samples which form a standard electrophoregram;
   detecting a peak point of an albumin fraction of the standard electrophoregram;
   detecting a peak point of a $\beta$-globulin fraction of the standard electrophoregram on the basis of the peak point of the albumin fraction;
   detecting the peak point of the albumin fraction of test sample;
   detecting a peak point near a position which is separated from said peak point of albumin fraction of test sample by a distance which is equal to a distance between the peak points of the albumin and $\beta$-globulin fractions of the standard electrophoregram; and
   determining said peak point as the peak point of the $\beta$-globulin fraction of test sample.

6. A method according to claim 3, wherein said step of detecting the peak points of the albumin fraction and $\beta$-globulin fraction comprises
   comparing all the stored data samples with a threshold level to extract a series of data samples which exceed said threshold level;
   detecting one or more peak points of the extracted data samples within a predetermined range measured from one end of said series of extracted data samples;
   determining a peak point having the maximum value among the detected peak points as the peak point of the albumin fraction;
   detecting one or more peak points within a predetermined range set on the basis of the other end of said series of extracted data samples; and
   determining a peak point having the maximum value among the detected peak points as the peak point of the $\beta$-globulin fraction.

7. A method according to claim 6, wherein said threshold level is so determined that the series of extracted data samples substantially constitute the electrophoregram.

8. A method according to claim 3, further comprising a step of normalizing values of said stored data samples on the basis of a ratio of the number of stored data samples between said peak points to the number of data samples between said two predetermined points on the electrophoregram.

9. A method according to claim 8, wherein said normalizing step comprises
   multiplying the values of the stored data samples by said ratio.

10. A method according to claim 8, further comprising
    a step of normalizing values of the stored data samples on the basis of at least one accumulation value of a fraction of a component in the serum sample and a concentration value of the relevant component, which concentration value is measured separately from the electrophoresis.

11. A method according to claim 10, wherein said normalizing step comprises
    deriving an accumulation value of a normalized albumin fraction;
    multiplying a concentration value of albumin by a predetermined reference accumulation value to derive a normalized concentration value;
    deriving a ratio of the normalized concentration value to the normalized accumulation value; and
    multiplying respective values of data samples by said ratio.

12. The method according to claim 10, wherein said concentration value is a concentration value of total protein of the sample.

13. A method according to claim 1, further comprising printing the electrophoregram of the test sample on a test report bearing a record of pattern related to a standard electrophoregram of normal sample.

14. A method according to claim 13, wherein said record of pattern on the test report comprises the standard electrophoregram of normal sample.

15. A method according to claim 14, wherein said standard electrophoregram is recorded by a line different from a line of the electrophoregram of the test sample to be printed.

16. A method according to claim 13, wherein said pattern comprises a pattern representing a normal range related to the standard electrophoregram of normal sample.

17. A method according to claim 14, wherein said pattern representing the normal range is recorded by a line different from a line of the electrophoregram of the test sample to be printed.

18. A method of processing a test sample comprising the steps of:
photoelectrically scanning an electrophoretic image of the test sample to derive an electrophoretic image signal;
sampling the electrophoretic image signal to derive a number of data samples;
storing said samples in a memory of a digital computer;
referencing said stored data samples to detect at least two reference points on the electrophoretic image;
generating a pattern related to a standard electrophoregram of a normal sample;
normalizing an electrophoretic expansion length of the electrophoregram of the test sample by adjusting said reference points to make said reference points coincident with at least two predetermined points on an electrophoregram having a predetermined electrophoretic expansion length; and
displaying the electrophoregram of the test sample having the normalized electrophoretic expansion length and said pattern in a superimposed manner on a monitor of said digital computer.

19. A method according to claim 18, wherein said step of deriving the pattern related to the standard electrophoregram of normal sample comprises:
subjecting the normal sample to electrophoresis on a substrate which is the same as a substrate on which the electrophoretic image of the test sample is formed to form a standard electrophoretic image;
scanning photoelectrically the standard electrophoretic image of normal sample to derive a standard electrophoretic image signal;
sampling the standard electrophoretic image signal to derive standard data samples of the normal sample; and
normalizing the standard data samples to derive a normalized standard electrophoregram of normal sample.

20. A method according to claim 19, wherein said standard electrophoregram of normal sample is displayed by a line which is different from a line of the electrophoregram of test sample.

21. A method according to claim 18, wherein said step of deriving the pattern related to the standard electrophoregram of normal sample comprises deriving a pattern representing a normal range related to the standard electrophoregram of normal sample.

22. A method according to claim 21, wherein said normal range is derived from the standard electrophoregram of normal sample.

23. A method of processing an electrophoregram of a test sample, comprising the steps of:
storing said electrophoregram in a first memory of a digital computer;
normalizing th stored electrophoregram by a method comprising referencing said stored electrophoregram to detect at least two reference points and adjusting said at least two reference points to make said at least two reference points coincident with at least two predetermined points on an electrophoregram having a predetermined electrophoretic expansion length;
storing said normalized electrophoregram in a second memory of said computer;
comparing the stored normalized electrophoregram with a standard electrophoregram to derive at least one pattern; and
displaying or printing said stored normalized electrophoregram and said pattern one upon the other such that respective measuring points of the pattern are aligned with corresponding measuring points of the stored normalized electrophoregram of the test sample on an appropriate I/O device of said computer.

24. A method according to claim 23, wherein said normalizing step further comprises:
measuring a total amount of substances in the test sample to be tested; and
normalizing the electrophoregram of the test sample having a normalized electrophoretic expansion length on the basis of said total amount of substances such that an accumulation value of the electrophoregram of the test sample is made proportional to said total amount of substances.

25. A method according to claim 24, wherein said normalizing step further comprises
deriving the number of stored data samples between said at least two reference points;
deriving a ratio of said number of stored data samples between said at least two reference points to the number of data samples between said at least two predetermined points on the electrophoregram having the predetermined electrophoretic expansion length; and
multiplying respective data samples by said ratio.

26. A method according to claim 23, wherein said comparing step comprises
deriving a series of data samples of the electrophoregram of the test sample;
deriving a series of data samples of the standard electrophoregram of normal sample; and
deriving differences ($DELTA_i$) between said series of data samples of the electrophoregram of the test sample and said series of data samples of the standard electrophoregram of normal sample at respective measuring points (i).

27. A method according to claim 23, wherein said comparing step comprises
deriving a series of data samples of the electrophoregram of the test sample;
deriving a series of data samples of the standard electrophoregram of normal sample; and deriving ratios (RATIO$_i$) of said series of data samples of the electrophoregram of the test sample to said series of data samples of the standard electrophoregram of normal sample at respective measuring points.

28. A method according to claim 23, wherein said comparing step comprises
deriving a series of data samples of the electrophoregram of the test sample;
deriving a series of data samples of the standard electrophoregram of normal sample;
deriving a series of values (NR$_i$) representing a normal range;
deriving differences (DELTA$_i$) between said series of data samples of the electrophoregram of the test sample and said series of data samples of the standard electrophoregram of normal sample at respective measuring points; and
deriving ratios (NRATIO$_i$) of said differences to said series of values representing the normal range at respective measuring points.

29. A method according to claim 23, wherein said standard electrophoregram of normal sample is displayed or printed in superimposition with the electrophoregram of the test sample.

30. A method according to claim 23, wherein said standard electrophoregram of normal sample is derived by subjecting a normal sample to electrophoresis on a substrate which is the same as a substrate on which the test sample is subjected to electrophoresis.

31. A method according to claim 23, wherein said standard electrophoregram of normal sample is obtained by processing statistically a number of electrophoregrams of a number of test samples.

32. A method of processing a test sample, comprising:
subjecting the test sample to electrophoresis to form an electrophoretic image on a substrate;
scanning photoelectrically the electrophoretic image to derive an electrophoretic image pattern;
sampling the electrophoretic image pattern to derive a series of data samples representing an electrophoregram of the test sample;
storing said series of data samples in a first memory of a digital computer;
processing said stored series of data samples to derive a series of normalized data representing a normalized electrophoregram of the test sample;
storing said normalized series of data in a second memory of said computer;
referencing said stored normalized series of data to calculate a peak value of the normalized electrophoregram of the test sample within a predetermined range corresponding to the distance between the $\beta$-fraction and the $\gamma$-fraction;
comparing said peak value to a predetermined threshold value SL$_1$; if the peak value is equal to or smaller than SL$_1$, determining that there is no M-protein peak and ending the process, and if the peak value is larger than SL$_1$, carrying out the next step;
calculating a half-width of the peak value, and comparing the half-width of the detected peak value with upper and lower limits SL$_2$ and SL$_3$; if the half-width is out of a range between SL$_2$ and SL$_3$, determining that there is no M-protein peak and ending the process, and if the half-width is within said range, carrying out the next step;

comparing the peak value with another threshold value SL$_4$ which is larger than SL$_1$; if the peak value is equal to or smaller than SL$_4$, determining that there is a possibility that the relevant electrophoregram might include M-protein peak, and if the peak value is larger than SL$_4$, carrying out the next step;
detecting a data position of the peak;
comparing sample values of data points near the detected peak point with a stored normal range; if one or more values are below the stored normal range, determining that the M-protein is malignant, and if the sample values are in the stored normal range, determining that the M-protein is benign.

33. A method of processing a test sample, comprising:
subjecting the test sample to electrophoresis to form an electrophoretic image on a substrate;
scanning photoelectrically image to derive an electrophoretic image pattern;
sampling the electrophoretic image pattern to derive a series of data samples representing an electrophoregram of the test sample;
storing said series of data samples in a first memory of a digital computer;
processing said stored series of data samples to derive a series of normalized data samples representing a normalized electrophoregram of the test sample;
storing said normalized data samples in a second memory of said computer;
referencing said stored normalized data samples to detect peak points of $\beta$- and $\gamma$-fractions of the normalized electrophoregram of the test sample;
extracting a portion of the stored normalized data samples between the detected peak points of the $\beta$- and $\gamma$-fractions;
comparing said extracted normalized data samples with a predetermined normal range; if any one of the extracted normalized data samples does not exceed the normal range, determining that $\beta$-$\gamma$ bridging does not exist and ending the process, and if one of he extracted normalized data samples exceeds the normal range, carrying out the next step;
comparing a width of a portion of the normalized data samples which exceeds the predetermined normal range to a predetermined normal width; if the width of the extracted data samples does not exceed the normal width, determining that there is no $\beta$-$\gamma$ bridging and ending the process, and if the width of the extracted data samples exceeds the normal width, carrying out the next step; and
judging whether a M-protein peak exists within the portion of data samples exceeding the normal range; if the M-protein peak is detected, determining that no $\beta$-$\gamma$ bridging exists, but if the M-protein is not detected, determining that $\beta$-$\gamma$ bridging exists.

34. A method of processing a test sample, comprising:
subjecting the sample to electrophoresis to form an electrophoretic image on a substrate;
sampling the electrophoretic image pattern to derive a series of data samples representing an electrophoregram of the test sample;
storing said series of data samples in a first memory of a digital computer;
referencing said stored series of data samples to derive a series of normalized data samples representing a normalized electrophoregram of the test sample;

storing said normalized data samples in a second memory of said computer;

comparing one or more of said stored normalized samples situated on the positive polarity side with respect to the albumin peak point to a predetermined normal range; if all the normalized samples do not exceed the normal range, determining that there is no leading and ending the process, but if at least one stored normalized data sample exceeds the normal range, carrying out the next step;

calculating a judgment value which represents a degree of symmetry of the albumin fraction; and comparing said judgment value to a predetermined normal range; if the judgment value does not exceed the normal range, determining that there is no leading, but if the judgment value exceeds the normal range, determining that leading exists on the positive polarity side of the albumin fraction.

* * * * *